United States Patent [19]

Takayanagi et al.

[11] 4,433,142
[45] Feb. 21, 1984

[54] PROCESS FOR THE PREPARATION OF 7-(2-AMINO-2-PHENYLACETAMIDO) CEPHEM DERIVATIVES

[75] Inventors: Keizo Takayanagi, Gumma; Yasuhide Tanaka, Saitama; Tasuke Kawabata, Saitama; Fujio Nakamura, Saitama; Yukio Morita, Saitama; Shigeto Negi, Tokyo; Takeo Kanai; Eiichi Morita, both of Saitama, all of Japan

[73] Assignee: Eisai Co., Ltd., Japan

[21] Appl. No.: 376,214

[22] Filed: May 7, 1982

[30] Foreign Application Priority Data

May 15, 1981 [JP] Japan .................................. 56-72173

[51] Int. Cl.³ .................. C07D 501/04; C07D 544/29
[52] U.S. Cl. ........................................ 544/26; 544/29; 424/246
[58] Field of Search ...................... 544/26, 27; 424/246

[56] References Cited

U.S. PATENT DOCUMENTS 4,148,817  4/1979  Wright .................................. 544/26

Primary Examiner—Nicholas S. Rizzo
Attorney, Agent, or Firm—Wenderoth, Lind & Ponack

[57] ABSTRACT

Improved process for the preparation of 7-(2-amino-2-phenyl-acetamido)cephem derivatives of the general formula (I):

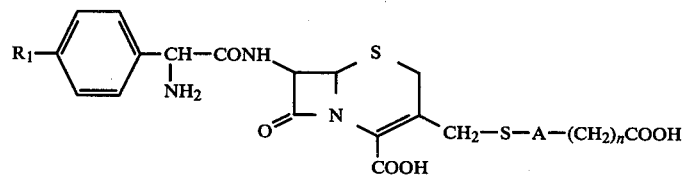

wherein $R_1$ is a hydrogwn atom or hydroxyl group, n stands for 0, 1 or 2, and A denotes a nitrogen-containing heterocyclic group or a direct bond coupling directly the sulfur atom and the $-(CH_2)_n COOH$ group together, as well as pharmaceutically acceptable salts thereof. The process is not only simple and easy to carry out, but also provides as crystalline precipitate the intended products with a high yield. The 7-(2-amino-2-phenyl-acetamido)cephem derivatives are useful as intermediates for syntheses of antibacterial agents.

12 Claims, No Drawings

PROCESS FOR THE PREPARATION OF 7-(2-AMINO-2-PHENYLACETAMIDO) CEPHEM DERIVATIVES

BACKGROUND OF THE INVENTION

This invention relates to a process for preparing a compound represented by the general formula (I):

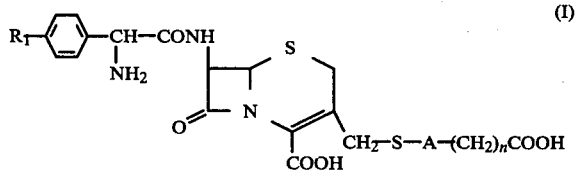

wherein $R_1$ is a hydrogen atom or hydroxyl group, n stands for 0, 1 or 2, and A denotes a nitrogen-containing heterocyclic group or a direct bond coupling directly the sulfur atom and the $-(CH_2)_nCOOH$ group together or a pharmaceutically acceptable salt thereof. More specifically, it relates to a process for preparing the compound of the general formula (I) or its pharmaceutically acceptable salt by reacting its corresponding phenylglycine derivative with 7-aminocephem derivative.

The compounds obtained in accordance with the process of this invention are useful as synthesis intermediates for antibacterial agents. The amino groups of the compounds of the general formula (I) may be acylated in a conventional manner, for example, those disclosed in Japanese Patent Application Laid-open No. 5487/1981, to prepare antibacterial agents.

Japanese Patent Application Laid-open No. 54580/1976 discloses a prior art preparation process of a compound represented by the general formula (I) by reacting its corresponding phenylglycine derivative with 7-aminocephem derivative. According to the above prior art process, N-t-butoxycarbonyl-p-hydroxyphenylglycine is reacted with 7-amino-3-(1-carboxymethyltetrazol-5-ylthiomethyl)-3-cephem-4-carboxylic acid and the protecting group is then removed from the resultant reaction product to give 7-(α-amino-4-hydroxyphenylacetamido)-3-(1-carboxymethyltetrazol-5-ylthiomethyl)-3-cephem-4-carboxylic acid. In other words, the p-hydroxyphenylglycine is caused to undergo a reaction after its amino group has been protected with a t-butoxycarbonyl group. According to the above known literature, the above prior art process provided an extremely low yield, i.e., a yield of as low as about 5%.

It has also been known from U.S. Patent Specification No. 4,148,817 and Japanese Patent Application Laid-open No. 87189/1977 to obtain certain cephalosporin-type compounds by first reacting phenylglycine derivatives, whose amino groups have been protected in the enamine forms, with 7-aminocephem derivatives, removing the protecting groups using hydrochloric acid or nitric acid and then obtaining the cephalosporin-type compounds through their isoelectric point precipitation, although the cephalosporin-type compounds are different from the compounds represented by the general formula (I). The above preparation method was also tried in the initial stage of the present inventors' research on the syntheses of the compounds produced by the process of this invention. It was however found that, in the course of the isoelectric point precipitation after the removal of the enamine-form protection, intended products adhered as sticky substances on the reaction vessels and their post-treatment was indispensable to obtain them in crystalline form, thereby leading to lowered yields.

SUMMARY OF THE INVENTION

With the foregoing in view, the present inventors have carried out an extensive research to improve the above process. As a result, the present inventors have unexpectedly found a simple and efficient process wherein a mere addition of water instead of nitric acid or hydrochloric acid in the removal step of the enamine-form protection is capable of successfully removing the amino-protecting group and providing as crystalline precipitate the intended product with a high yield.

Accordingly, the present invention provides in one aspect thereof a process for preparing a 7-(2-amino-2-phenylacetamido)cephem derivative represented by the general formula (I):

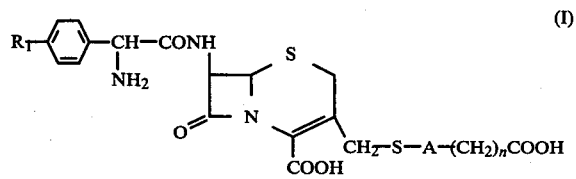

wherein $R_1$ is a hydrogen atom or hydroxyl group, n stands for 0, 1 or 2, and A denotes a nitrogen-containing heterocyclic group or a direct bond coupling directly the sulfur atom and the $-(CH_2)_nCOOH$ group together or a pharmaceutically acceptable salt thereof, which process comprises the following consecutive steps:

(a) reacting a compound of the general formula (II):

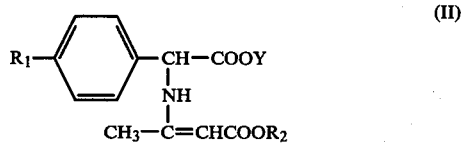

wherein $R_1$ has the same significance as defined above, $R_2$ means a lower alkyl and Y represents an alkali metal with a chloroformate;

(b) reacting the reaction product of step (a) with a compound having the general formula (III):

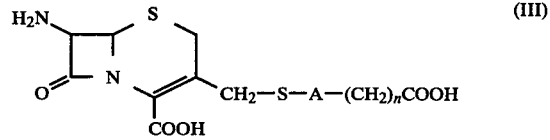

wherein n and A have the same meaning as defined above or its salt; and (c) subjecting the reaction product of step (b) to hydrolysis by adding water thereto.

When the pharmaceutically acceptable salt is desired, the reaction product of step (c) may be converted into the same salt by a method known per se in the art.

The process according to this invention is simple and easy to carry out and is capable of providing 7-(2- amino-2-phenylacetamido)cephem derivatives with rather high yield.

The above and other objects, features and advantages of the present invention will become apparent from the following description and the appended claims.

DETAILED DESCRIPTION OF THE INVENTION AND PREFERRED EMBODIMENTS

Although the present invention may be defined in a broad aspect as described above, exemplary lower alkyl groups($R_2$) may include methyl, ethyl, i-propyl, n-propyl, t-butyl and like groups. As the alkali metal(Y), may be mentioned sodium, potassium or the like. As exemplary nitrogen-containing heterocyclic groups(A), may be mentioned tetrazolyl, 1,3,4-thiadiazolyl, 1,3,4-oxadiazolyl, 1,2,3-triazoyl, 1,3,4-triazolyl and their analogous groups. On the other hand, as the pharmaceutically acceptable salt of the compound of the general formula (I), may be mentioned its alkali metal salt such as sodium salt or potassium salt as a carboxylic acid salt or its acid salt such as trifluoroacetic acid salt and the like as a salt with reference to amino group.

In the above process, the reaction of each of steps (a) and (b) may be carried out using as a reaction solvent acetonitrile, dimethylformamide, dichloromethane, ethyl acetate, chloroform, tetrahydrofuran, formamide, dimethylsulfoxide, dimethylacetamide or a mixture thereof.

Except for the case of providing the starting materials as solutions in a solvent, it is desirable to carry out the reaction of each of steps (a) and (b) at temperatures in the range of from −50° C. to room temperature.

Upon carrying out the reaction of each of steps (a) and (b), it is also desirous to block the hydroxyl group of the compound of the general formula (II) and the carboxyl groups of the compound of the general formula (III) by suitable protecting groups. Conventionally known protecting groups may be used. However, a particularly preferred protecting group is a silyl group for the reasons that it can protect both hydroxyl group and carboxyl groups and it can be readily removed. As silylating reagents, there may be mentioned for example monotrimethylsilylacetamide, bis(trimethylsilyl)acetamide, hexamethyldisilazane, trimethylsilylchloride and the like. For removing the silyl group after the reaction of step (b), may be employed a lower alkyl alcohol such as methanol, ethanol, i-propanol or the like, water, an aqueous lower alkyl alcohol or the like.

It is desirable to conduct the reaction of step (a), i.e., the reaction between the compound of the general formula (II) and the chloroformate in the presence of a tertiary amine such as N,N-dimethylbenzylamine, N,N-dimethylaniline, N-methylmorpholine, triethylamine or the like in order to accelerate the reaction. Exemplary chloroformates include lower alkyl chloroformates such as ethyl chloroformate, methyl chloroformate, i-butyl chloroformate and the like as well as chlorinated lower alkyl chloroformates such as trichloroethyl chloroformate, etc.

The reaction of step (b), in other words, the reaction between the reaction product of the compound of the general formula (II) and chloroformate with the compound of the general formula (III) may be conducted in either presence or absence of an acid. As such an acid, may be mentioned for instance methanesulfonic acid, p-toluenesulfonic acid, benzenesulfonic acid, trifluoroacetic acid, formic acid, or the like.

After the completion of the reaction of step (b), protecting groups are removed from the reaction product of step (b) whenever its hydroxyl group and carboxyl groups are blocked. Then, its enamine protection is removed by adding water to the reaction mixture resulted from step (b) or from the removal step of the protecting groups when the hydroxyl and carboxyl groups were blocked by the protecting groups, thereby removing the enamine protection and obtaining the intended product of the general formula (I) as crystalline precipitate.

The following examples illustrate this invention, but are not to be construed as limiting the scope thereof.

EXAMPLE 1

7β-[D-2-Amino-2-(4-hydroxyphenyl)acetamido]-3-(1-carboxymethyl-5-tetrazolyl)thiomethyl-3-cephem-4-carboxylic acid Potassium D(−)-α-(1-methoxycarbonyl-1-propene-2-yl)amino-p-hydroxyphenylacetate (7.89 g), acetonitrile (150 ml) and monotrimethylsilylacetamide (5.25 g) were heated under a nitrogen gas stream to about 70° C. so as to obtain a solution. The solution was then cooled to −25° C., followed by addition of N,N-dimethylbenzylamine (0.0014 ml) and then ethyl chloroformate (2.96 g) in acetonitrile (3 ml). The resulting mixture was stirred at the same temperature for 1 hour, thereby providing "Solution A".

7β-Amino-3-(1-carboxymethyl-5-tetrazolyl)thiomethyl-3-cephem-4-carboxylic acid (7.45 g), acetonitrile (129 ml) and monotrimethylsilyacetamide (11.8 g) in acetonitrile (10 ml) were stirred at 20° C. to obtain a solution. The resulting solution was then cooled to −10° C., thereby providing "Solution B."

To Solution A was added formamide (20 ml), and Solution B was then added dropwise to the former solution, followed by stirring the resulting mixture at about −25° C. for 2 hours. To the reaction mixture, was added methanol (5.7 ml). The resulting reaction mixture was heated to 10° C. and then stirred for 30 minutes. Insoluble matter was filtered off and water (4 ml) was added to the filtrate, followed by stirring them at room temperature overnight. The resulting crystalline mass was collected through filtration and then dried, thereby obtaining the intended product (8.35 g) (yield: 80%).

IR spectrum($cm^{-1}$), nujol): 1755–1770, 1685, 1610.

NMR spectrum(δ, DMSO-$d_6$-$D_2O$) 3.42(1H, d, J=19 Hz), 3.65(1H, d, J=19 Hz), 4.19(2H, br.s), 4.7–5.1(4H, m), 5.69(1H, d, J=5 Hz), 6.81(2H, d, J=8.5 Hz), 7.30(2H, d, J=8.5 Hz).

EXAMPLE 2

7β-[D-2-Amino-2-(4-hydroxyphenyl)acetamido]-3-(1-carboxymethyl-5-tetrazolyl)thiomethyl-3-cephem-4-carboxylic acid To acetonitrile (150 liters) was suspended potassium D(−)-α-(1-methoxycarbonyl-1-propene-2-yl)amino-p-hydroxyphenylacetate (7.89 kg). Monotrimethylsilylacetamide (5.25 kg) was dissolved in acetonitrile (5 liters). The resulting solution was then added to the above suspension, and the whole was agitated at 70° C. under a nitrogen gas stream. The thus-prepared solution was cooled to −26° C. and added successively with N,N-dimethylbenzylamine (1.4 ml) in acetonitrile (100 ml) and then ethyl chloroformate (2.96 Kg) in acetonitrile (3 liters). The resulting mixture was stirred at the same temperature for 1 hour and 30 minutes, thereby providing "Solution A."

7β-Amino-3-(1-carboxymethyl-5-tetrazolyl)thiomethyl-3-cephem-4-carboxylic acid (7.45 Kg), acetonitrile (129 liters), monotrimethylsilyl acetamide (15.4 kg) and methane sulfonic acid (961 g) in acetonitrile (1 liter) were mixed at 20° C. to obtain the solution which in turn cooled to −10° C., thereby providing "Solution B".

To Solution A were successively added formamide (20 liters) and then Solution B. After stirring them for 1 hour and 30 minutes, methanol (7 liters) were added, followed by further stirring at 10° C. for 1 hour. Insoluble matter was filtered off. To the filtrate was added water (4 liters). The resultant mixture was stirred at room temperature overnight. The resulting crystalline precipitate was collected through filtration and dried, thereby obtaining the intended product (8.1 kg) (yield: 77.7%).

IR and NMR spectra of the thus-obtained compound were in conformity with those obtained in Example 1.

EXAMPLE 3

7β-[D-2-Amino-2-(4-hydroxyphenyl)acetamido]-3-[5-carboxymethyl-2-(1,3,4-thiadiazolyl)]thiomethyl-3-cephem-4-carboxylic acid In a nitrogen gas stream, were agitated at 78° C. potassium D(−)-α-(1-methoxycarbonyl-1-propene-2-yl)amino-p-hydroxyphenylacetate (1.79 g), monotrimethylsilylacetamide (1.19 g), and acetonitrile (35.8 ml) to form solution. The resulting solution was cooled to −25° C., and successively added N,N-dimethylbenzylamine (1 mg) and then ethyl chloroformate (0.67 g) in acetonitrile (5 ml). The resulting mixture was stirred at the same temperature for 1 hour, thereby providing "Solution A."

At 20° C., were stirred 7β-amino-3-[5-carboxymethyl-2-(1,3,4-thiadiazolyl)]thiomethyl-3-cephem-4-carboxylic acid (1.8 g), monotrimethylsilylacetamide (3.7 g), methane sulfonic acid (0.24 g) and acetonitrile (31 ml) to give a solution, which was thereafter cooled to 5° C. to provide "Solution B".

To Solution A was successively added formamide (4.4 ml) and then Solution B. After agitating the resultant mixture at −25° C. for 2 hours, methanol (1.6 ml) was added thereto. The resulting mixture was then agitated at room temperature for further one hour. Insoluble matter was filtered off and water (0.9 ml) was added to the filtrate. The resultant filtrate was agitated at room temperature for 2 hours. The resulting crystalline precipitate was collected through filtration and then dried, thereby obtaining the intended product (1.75 g) (yield: 70.7%).

IR spectrum(cm$^{-1}$, nujol): 1760, 1690, 1610.

NMR spectrum(δ, DMSO-d$_6$) 4.25(1H, d, J=16 Hz), 4.52(1H, d, J=16 Hz), 4.15(2H, s), 4.90(1H, s), 5.02(1H, d, J=4.5 Hz), 5.6–5.84(1H, m), 6.80(2H, d, J=8 Hz), 7.34(2H, d, J=8 Hz).

EXAMPLE 4

7β-[D-2-Amino-2-(4-hydroxyphenyl)acetamido]-3-(1-carboxymethyl)thiomethyl-3-cephem-4-carboxylic acid In a nitrogen gas stream, were stirred at 80° C. potassium D(−)-α-(1-methoxycarbonyl-1-propene-2-yl)amino-p-hydroxyphenylacetate (3.58 g), monotrimethylsilylacetamide (2.38 g) in acetonitrile (4 ml), and acetonitrile (71 ml) to form solution, which was then cooled to −25° C. To the thus-cooled solution was added successively N,N-dimethylbenzylamine (2 mg) and ethyl chloroformate (1.34 g) in acetonitrile (10 ml), followed by stirring at the same temperature for 2 hours to provide "Solution A".

At 30° C., were agitated 7β-amino-3-(1-carboxymethyl)thiomethyl-3-cephem-4-carboxylic acid (2.79 g), monotrimethylsilylacetamide (15.4 g), methane sulfonic acid (0.48 g) and acetonitrile (32 ml) to give a solution, followed by cooling the same solution to 10° C. to provide "Solution B".

To Solution A was added successively formamide (8.8 ml) and then Solution B. The resultant mixture was stirred at −25° C. for 1 hour and 10 minutes and methanol (3.2 ml) was added thereto. The thus-prepared mixture was agitated at room temperature for further one hour. Insoluble matter was filtered off, and water (1.8 ml) was added to the filtrate. The resulting solution was heated to 35° C. and stirred overnight at room temperature. The resulting crystalline precipitate was collected through filtration and dried, thereby obtaining the intended product (2.57 g) (yield: 61.8%).

IR spectrum(cm$^{-1}$, nujol): 1760, 1680, 1610.

NMR spectrum(δ, DMSO-d$_6$): 3.05–3.95(6H, m), 4.86(1H, s), 4.95(1H, d, J=4.5 Hz), 5.5–5.7(1H, m), 6.78(2H, d, J=8 Hz), 7.32(2H, d, J=8Hz).

EXAMPLE 5

7β-[D-2-Amino-2-(4-hydroxyphenyl)acetamido]-3-[5-carboxymethyl-2-(1,3,4-oxadiazolyl)]thiomethyl-3-cephem-4-carboxylic acid In a nitrogen gas stream and at 74° C., were stirred potassium D(−)-α-(1-methoxycarbonyl-1-propene-2-yl)amino-p-hydroxyphenylacetate (2.63 g), monotrimethylsilylacetamide (1.75 g) in acetonitrile (2 ml) and acetonitrile (50 ml) to give a solution, which was then cooled to −25° C. To the thus-cooled solution was then successively added N,N-dimethylbenzylamine (1.5 mg) and ethyl chloroformate (1 g), followed by stirring it at the same temperature for 1 hour and 10 minutes to provide "Solution A."

At 30° C., were stirred 7β-amino-3-[5-carboxymethyl-2-(1,3,4-oxadiazolyl)]thiomethyl-3-cephem-4-carboxylic acid (2.5 g), methane sulfonic acid (320 mg), monotrimethylsilylacetamide (5 g) and acetonitrile (43 ml) to form solution, which was thereafter cooled to 5° C. to provide "Solution B".

To Solution A was successively added formamide (7 ml) and then Solution B, followed by stirring them at −25° C. for 1 hour and 30 minutes. To the resulting mixture was thereafter added methanol (2.5 ml), and the whole was then stirred at room temperature for further 30 minutes. Insoluble matter was filtered off, and water (1.3 ml) was added to the filtrate, followed by stirring the resultant mixture overnight at room temperature. The resulting crystalline mass was collected through filtration and dried to give the intended product (2.63 g) (yield: 75.1%).

IR spectrum(cm$^{-1}$, nujol): 1765, 1690, 1610.

NMR spectrum(δ, DMSO-d$_6$): 3.86(2H, s), 4.16(1H, d, J=14 Hz), 4.28(1H, d, J=14 Hz), 4.91(1H, s), 4.95(1H, d, J=4.5 Hz), 5.52–5.80(1H, m), 6.78(2H, d, J=8 Hz), 7.30(2H, d, J=8 Hz).

Having now fully described the invention, it will be apparent to one of ordinary skill in the art that many changes and modifications can be made thereto without departing from the spirit or scope of the invention as set forth herein.

What is claimed is:

1. A process for preparing a 7-(2-amino-2-phenylacetamido)cephem derivative represented by the formula (I):

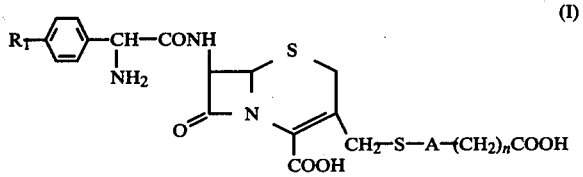

wherein $R_1$ is a hydrogen atom or hydroxyl group, n stands for 0, 1 or 2, and A denotes tetrazolyl, 1,3,4-thiadiazolyl, 1,3,4-oxadiazolyl, 1,2,3-triazolyl, or 1,3,4-triazolyl or a direct bond coupling directly the sulfur atom and the —$(CH_2)_n$COOH group together or a pharmaceutically acceptable salt thereof, which process consists essentially of the following consecutive steps:

(a) reacting a compound of the formula II:

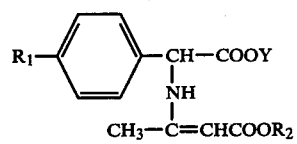

wherein $R_1$ has the same significance as defined above, $R_2$ means a lower alkyl and Y represents an alkali metal, with a chloroformate;

(b) reacting the reaction product of step (a) with a compound having the formula (III):

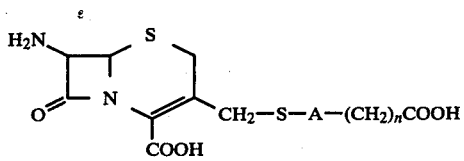

wherein n and A have the same meaning as defined above or its pharmaceutically acceptable salt; and (c) subjecting the reaction product of step (b) to hydrolysis by adding water thereto.

2. The process according to claim 1, wherein, when $R_1$ is a hydroxyl group in the compound of formula (I), the hydroxyl group of the compound of formula (II) is blocked by a protecting group prior to initiating the reaction of step (a) and the protecting group is removed after the completion of step (b), and both carboxyl groups of the compound of formula (III) are also blocked by protecting groups prior to proceeding with the reaction of step (b) and the protecting groups are removed after the completion of step (b).

3. The process according to claim 2, wherein all the protecting groups are silyl groups and their removal is effected in a medium selected from the group consisting of lower alkyl alcohols, water and mixtures thereof.

4. The process according to claim 3, wherein each of the compounds of formulae (II) and (III) is blocked at the hydroxyl group or carboxyl groups by reacting same with a silylating reagent selected from the group consisting of monotrimethylsilylacetamide, bis(trimethylsilyl)acetamide, hexamethylenedisilazane and trimethylsilylchloride.

5. The process according to claim 1, 2 or 3, wherein the reactions of steps (a) and (b) are carried out at temperatures in the range of from $-50°$ C. to room temperature and in an inert solvent selected from the group consisting of acetonitrile, dimethylformamide, dichloromethane, ethyl acetate, chloroform, tetrahydrofuran, formamide, dimethylsulfoxide, dimethylacetamide and mixtures thereof.

6. The process according to claim 1, 2 or 3, wherein the chloroformate is a lower alkyl chloroformate or a chlorinated lower alkyl chloroformate.

7. The process according to claim 1, 2 or 3, wherein the chloroformate is ethyl chloroformate, methyl chloroformate, i-butyl chloroformate or trichloroethyl chloroformate.

8. The process according to claim 1, 2 or 3, wherein the reaction of step (a) is carried out in the presence of a tertiary amine selected from the group consisting of N,N-dimethylbenzylamine, N,N-dimethylaniline, N-methylmorpholine and triethylamine.

9. The process according to claim 1, 2 or 3, wherein the reaction of step (b) is carried out in the presence of an acid selected from the group consisting of methanesulfonic acid, p-toluenesulfonic acid, benzenesulfonic acid, trifluoroacetic acid and formic acid.

10. The process according to claim 1, 2 or 3, wherein the pharmaceutically acceptable salt is an alkali metal salt or trifluoroacetic acid salt.

11. The process according to claim 1, 2 or 3, wherein A is a tetrazolyl, 1,3,4-thiadiazolyl, 1,3,4-oxadiazolyl, 1,2,3-triazolyl or 1,3,4-triazolyl group in the compound of formula (III) and, in the compound of formula (II), Y is sodium or potassium and $R_2$ is a methyl, ethyl, i-propyl, n-propyl or t-butyl group.

12. The process according to claim 1, 2 or 3, wherein $R_1$, $R_2$ and Y denote respectively —OH, —$CH_3$ and K in the compound of formula (II) and, in the compound of formula (III), n is 1.

* * * * *